United States Patent [19]

Schellenberger

[11] Patent Number: 5,756,316
[45] Date of Patent: May 26, 1998

[54] MOLECULAR CLONING BY MULTIMERIZATION OF PLASMIDS

[75] Inventor: Volker Schellenberger, Burlingame, Calif.

[73] Assignee: Genencor International, Inc., Rochester, N.Y.

[21] Appl. No.: 556,756

[22] Filed: Nov. 2, 1995

[51] Int. Cl.$^6$ .................................................. C12P 19/34
[52] U.S. Cl. .................. 435/912; 435/172.3; 435/252.31; 435/320.1
[58] Field of Search .......................... 435/172.1, 222, 435/221, 178.1, 320.1, 6, 91.2, 252.31, 172.3; 536/27, 23.2; 935/10, 19

[56] References Cited

U.S. PATENT DOCUMENTS

| | | | |
|---|---|---|---|
| 4,917,999 | 4/1990 | Byng et al. | 435/6 |
| 5,013,657 | 5/1991 | Bryan et al. | 435/172.3 |
| 5,273,902 | 12/1993 | Frischer et al. | 152/213 |
| 5,324,653 | 6/1994 | Van Eekelen et al. | 435/221 |

OTHER PUBLICATIONS

Horton et al. BioTechniques 8(5) 528–535. 1990.
Horton, R. 1995 Molecular Biotechnology (3) 93–99.
Old, RW and Primrose, SB 1985. pp. 162–163 and pp. 102–111.
Michel, et al., *Embo J.*, 1:1565–1571 (1982).
Mottes, et al., "Different Specific Activities of the Monomeric and Oligomeric Forms of Plasmit DNA in Transformation of B. Subtilis and E. Coli" *Molec. Gen. Genet.*, 174:281–286 (1979).
deVos, et al., "Plasmid Transformation in *Bacillus subtilis*: Fate of Plasmid DNA" *Mol. Gen. Genet.*, 181:424–433 (1981).
Weinrauch and Dubnau. "Plasmid Marker Rescue Transformation in *Bacillus subtilis*" *J. Of Bacteriology*, 154:1077–1087 (1983).
Yvette and Dubnau. "Plasmid Marker Rescue Transformation Proceeds by Breakage–Reunion in *Bacillus subtilis*" *J. Of Bacteriology*, 169:1205–1211 (1987).
Contente and Dubnau. "Marker Rescue Transformation by Linear Plasmid DNA in *Bacillus subtilis*" *Plasmid*, 2:555–571 (1979).

Haima, et al., "Novel Plasmid Marker Rescue Transformation System for Molecular Cloning in *Bacillus subtilis* Enabling Direct Selection of Recombinants" *Mol. Gen. Genet.*, 223:185–191 (1990).
Frischer, et al., "Natural Plasmid Transformation in a High–Frequency of Transformation Marine Vibrio: Variables Affecting Competency" *Abstr. Gen. Meet. Am. Soc. Microbiol,* (1992) 92 Meet., 390.
Frischer, M.E., "Effects of Environmental Parameters on Natural Plasmid Transformation of a High Frequency of Transformation Marine Vibrio" *Abstr. Gen. Meet. Am. Soc. Microbiol.* (1991) 91 Meet. 278.
Frischer, et al., "Natural Plasmid Transformation in a High–Frequency–of–Transformation Marine Vibrio Strain" *Appl. Environ. Microbiol.* (1990) 56(11):3439–3444.
Cantoral, et al., "Protoplast Transformation of Penicillium Chrysogenum Using Vector Carrying the pyr 4 Gene" *Eur. Congr. Biotechnol.* (1987) 1:512.
Pozzi, et al., "Transformation of *Streptococcus Sanguis* Challis with a Plasmid of *Streptococcus Pneumoniae*" *FEMS–Microbiol. Lett.* (1987) 48:1–2, 189–184.
Lindler, L.E. and F.L. Macrina, "Characterization of Genetic Transformation in Streptococcus Mutans by Using a Novel High–Efficiency Plasmid Marker Rescue System" *J. Bacteriol.*, (1986) 166(2):658–665.
Howell, S.H., and R.M. Walden, "The Response of Plants to in Vitro Modifications of the CaMV Genome" *J.Cell Biochem.*, (1983) Suppl. 7B:246.
Buzby, et al., "Plasmid Transformation in *Agmenellum Quadruplicatum* PR–6: Construction of Biphasic Plasmids and Characterization of their Transormation Properties" *J. Bacteriol.* (1983) 154(3):1446–1450.
McCarthy, D., "Plasmid Recombination in *Haemophilus influenzae*" *J. Mol. Biol.* (1982) 157:577–596.
GeneAmp brochure for XL PCR Kit, part No. N808–0182; rTth DNA Polymerase, XL & XL Buffer Pack, part No. N808–0180; Six Paq rTth DNA Polymerase, XL & XL Buffer Pack, part No. N808–0183, Perkin Elmer, pp. 1–19.

*Primary Examiner*—James Ketter
*Assistant Examiner*—Irem Yucel
*Attorney, Agent, or Firm*—Flehr Hohbach Test Albritton & Herbert LLP; Richard F. Trecartin; Robin M. Silva

[57] ABSTRACT

Novel methods of nucleic acid multimerization using PCR are provided, allowing direct transformation of cells and microorganisms.

37 Claims, 6 Drawing Sheets

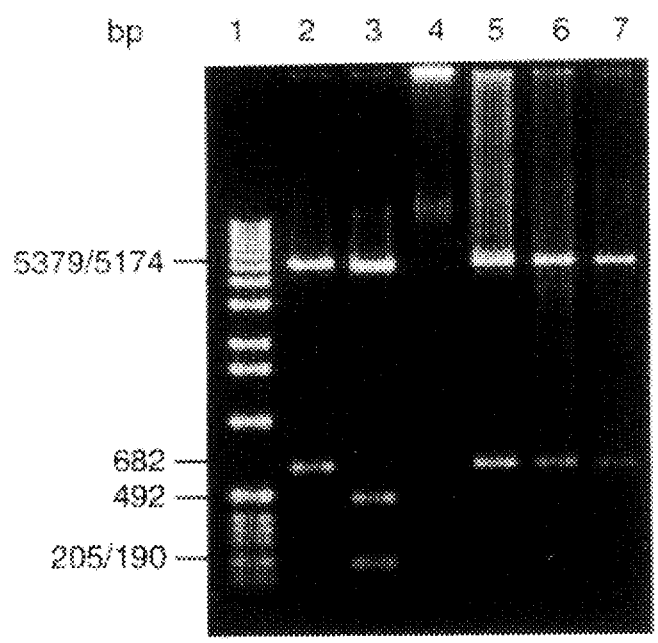
FIG._6

MOLECULAR CLONING BY MULTIMERIZATION OF PLASMIDS

FIELD OF THE INVENTION

Novel methods of nucleic acid multimerization using the polymerase chain reaction are provided which allow direct transformation of cells and microorganisms.

BACKGROUND OF THE INVENTION

The capacity to secrete many gene products into the growth medium makes *Bacillus subtilis* an interesting and important host for the production of enzymes and other proteins. However, the cloning and mutagenesis of genes in Bacillus is not as straightforward as similar processes in *E. coli*. While several small plasmids have been identified which are sufficiently stable in Bacillus, (see Molecular Biological Methods for Bacillus, Ed. Harwood and Cutting, John Wiley & Sons, 1990), a major obstacle to their broad application is the fact that plasmid monomers are not capable of transforming competent Bacillus cells to any significant degree. Accordingly, *E. coli* shuttle vectors are generally used, since these result in plasmid multimers which are then capable of transforming *B. subtilis*.

Unfortunately, these methods are inefficient and time consuming. In addition, it is particularly difficult to generate libraries of random mutants in Bacillus since this requires high transformation frequencies that are difficult to achieve with these methods. Furthermore, the passage through *E. coli* almost certainly introduces bias into the library, since some mutants will be enriched while others will be lost from the population.

Several strategies have been described in the literature for the direct cloning of DNA in Bacillus. Plasmid marker rescue transformation involves the uptake of a donor plasmid by competent cells carrying a partially homologous resident plasmid (Contente et al., *Plasmid* 2:555-571 (1979); Haima et al., *Mol. Gen. Genet.* 223:185-191 (1990); Weinrauch et al., *J. Bacteriol.* 154(3):1077-1087 (1983); and Weinrauch et al., *J. Bacteriol.* 169(3):1205-1211 (1987)). The incoming donor plasmid recombines with the homologous region of the resident "helper" plasmid in a process that mimics chromosomal transformation. Unfortunately, this method does not appear to be suitable for high-copy number plasmids because the helper plasmid persists in the transformed cells. This is significant because high-copy number plasmids are preferred for cloning as they generally lead to higher levels of expression of the encoded genes and result in simpler isolation of plasmid DNA for subsequent manipulations as compared to low-copy number plasmids.

Plasmid multimers used in the direct transformation of *B. subtilis* have been generated by ligation of plasmid monomers at very high concentrations (de Vos et al., *Mol. Gen. Genet.* 181:424-433 (1981), Mottes et al., *Molec. gen. Genet.* 174:281-286 (1979). This approach, however, requires large amounts of DNA and results in random orientation of the ligated fragments, due to the fact that restriction sites are generally palidromes.

Michel et al. reported the transformation of *B. subtilis* using monomers of plasmids containing internal repeats, but such constructs are prone to recombination under many conditions. (Michel et al., 1982 *EMBO J.* 1:1565-1571).

Thus, direct transformation of Bacillus species has been limited to methods requiring either large amounts of plasmid DNA or low-copy number plasmids.

Accordingly, it is an object of the invention to provide methods for the generation of plasmid multimers for the direct transformation of cells such as microorganisms, particularly Bacillus species such as *B. subtilis*.

It is an additional object to provide methods for the generation of cDNA and mutagenesis libraries in cells such as microorganisms, particularly Bacillus species.

SUMMARY OF THE INVENTION

The invention provides methods of generating nucleic acid multimers comprising contacting a first linear nucleic acid comprising a first end sequence, a second end sequence, and an intervening sequence with a second linear nucleic acid comprising a third end sequence homologous to said first end sequence and a fourth end sequence homologous to said second end sequence. The combined first and second linear nucleic acids form a mixture which is subjected to the polymerase chain reaction for at least three cycles to form multimeric nucleic acids. Such nucleic acid multimers may then be used to transform cells.

The methods of the invention can also be used to produce chimeric nucleic acids. In this method, the sequence of the third end sequence has at least one different nucleotide than the sequence of the first end sequence.

The methods of the invention can also be used to generate libraries in a microorganism. Such methods comprise generating a plurality of first nucleic acids each comprising a first end sequence, an intervening sequence and a second end sequence wherein said plurality of first nucleic acids comprise a population of library fragments. The plurality of first nucleic acids is contacted with a second nucleic acid comprising third and fourth end sequences homologous to the first and second end sequences, respectively, of at least one of the first nucleic acids. The mixture thus formed is subjected to conditions which permit the polymerase chain reaction for at least three cycles.

The invention also includes the multimeric nucleic acid made according to the methods of the invention as well as the cells and microorganisms transformed with such nucleic acid multimers.

BRIEF DESCRIPTION OF THE DRAWINGS

In FIG. 3, the end sequences of the first and second nucleic acid comprise a gene.

FIG. 6 shows a BamHI/XbaI digest of plasmid DNA. Lane 1, molecular weight marker (marker X, Boehringer); lane 2, pVS02; lane 3, pBS19; lane 4, PCR generated plasmid multimers, undigested; lane 5, PCR generated multimers, BamHI/XbaI digested; lane 6, plasmid DNA isolated from a halo forming clone; lane 7, plasmid DNA from a non-halo forming clone.

DETAILED DESCRIPTION OF THE INVENTION

Figure 1:
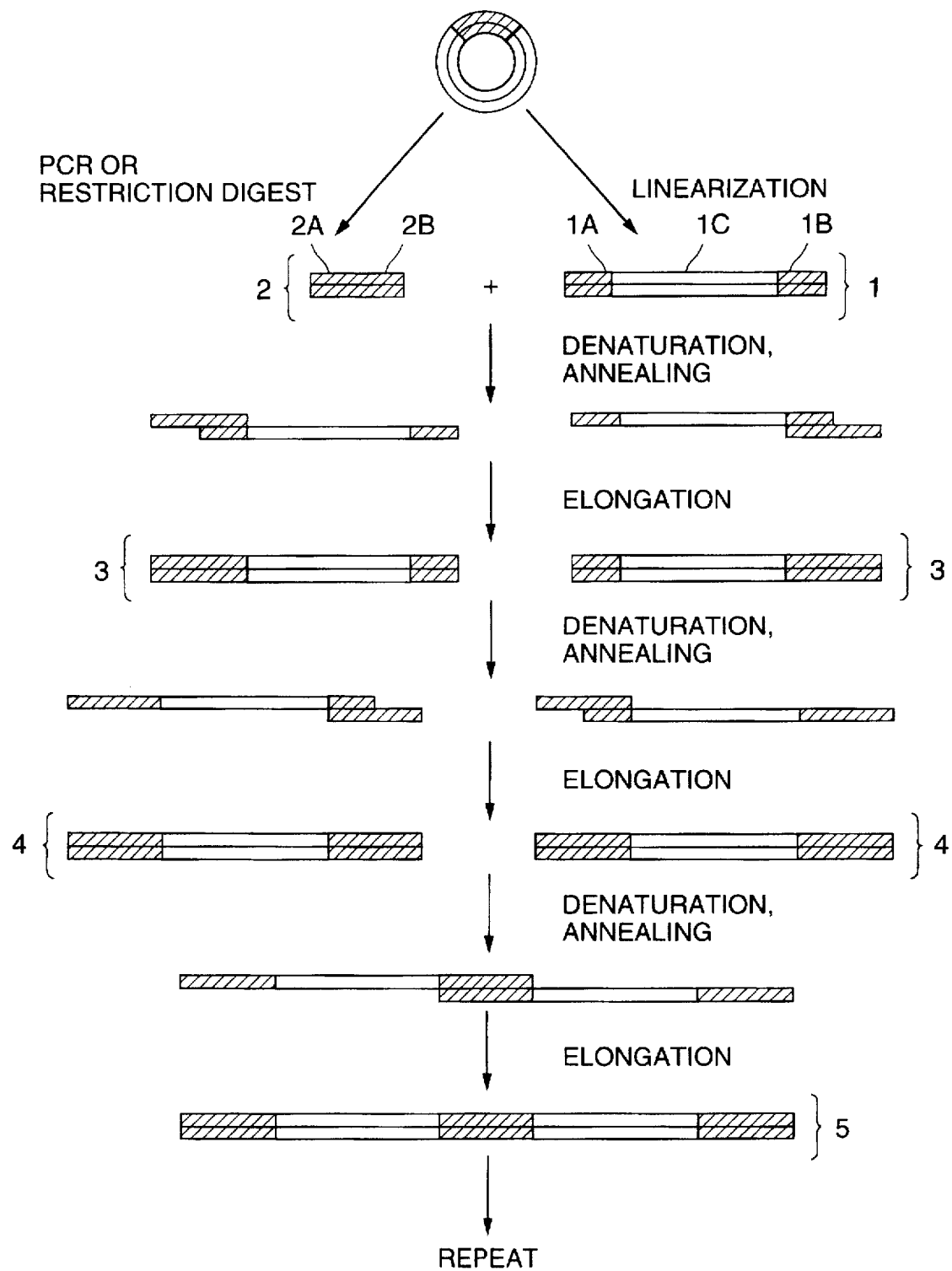
FIG. 1 is a schematic depiction of a general method of the invention using double stranded nucleic acids.

The invention provides methods and compositions which may be used for the transformation of certain cells, particularly microorganisms such as Bacillus species. The general method is most easily described using a double stranded embodiment schematically described in FIG. 1, although other embodiments are also contemplated using single stranded nucleic acids having similar end sequence regions. As is shown in FIG. 1 and in the following schematic, the method requires two separate nucleic acids. In FIG. 1, the end sequences of the first and second nucleic acid comprise a gene. The plasmid is depicted at the top, with the shaded region depicting a gene. Cleavage of the plasmid within the gene gives rise to the first nucleic acid (1), comprising a first end sequence (1A), an intervening sequence (1C), and a second end sequence (1B). The second nucleic acid (2), comprises a third end sequence (2B) and a fourth end sequence (2A).

sequence in the organism, containing a single copy of the gene of interest. This appears to be true even if the multimers contain a variety of different genes of interest, for example in the generation of a library or via mutagenesis of a particular gene. Thus, the present invention provides methods for direct transformation of Bacillus as well as methods for generating libraries in Bacillus. As will be described below, in some rare instances, the multimer forms used for transformation that contain different genes may result in Bacillus species that carry more than one gene of interest. However, in these instances, the number of different genes is low (less than five) and can be overcome by normal segregation mechanisms for replicating plasmids when grown for a period of time in the host organism.

Accordingly, the present invention is particularly useful in the transformation of Bacillus species such as B. subtilis,

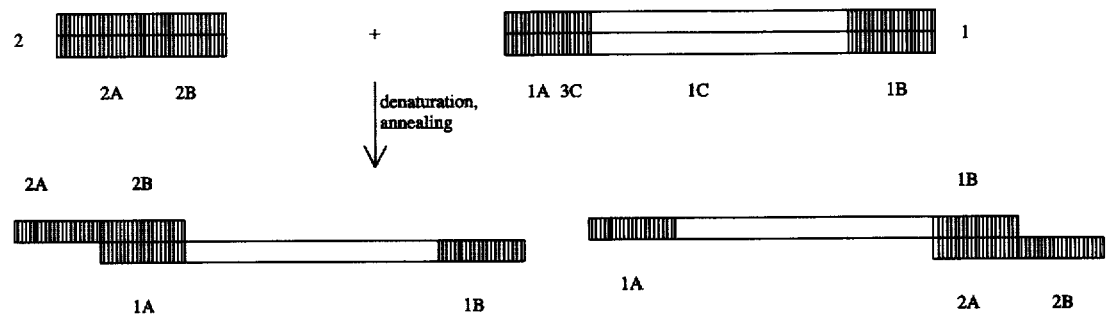

The second nucleic acid can be the gene cleaved from the plasmid or contain sequences which are capable of hybridizing to the first and second end sequences 1A and 1B of the first nucleic acid. Upon denaturation, the two strands of each nucleic acid separate, to anneal with the appropriate complementary strand of the other nucleic acid. That is, the first end sequence (1A) hybridizes with the third end sequence (2B), and the second end sequence (1B) hybridizes with the fourth end sequence (2A). Elongation via primer extension yields partially extended first nucleic acids (3). Repeating the cycle yields the extended first nucleic acids (4). Additional cycles yield multimeric forms of the first nucleic acid (5), with (5) comprising two monomers. Repeating the PCR cycling process results in long multimers of the first and second nucleic acids, as well as multimeric aggregates, as is more fully described below. These multimers are then used to transform cells at very high efficiencies.

The methods of the invention find particular use in Bacillus species, due to the mechanism of uptake of exogeneous nucleic acid by such organisms. Without being bound by theory, it appears that certain organisms, such as Bacillus, do not take up and express monomeric plasmids or vectors.

Instead, plasmid multimers must be used, which allow the uptake of nucleic acid by competent microorganisms such as Bacillus species. The uptake of nucleic acid by competent Bacillus species is thought to occur as a result of a "nick" that is generated by the Bacillus. The microorganism nicks the nucleic acid and then pulls it into the organism from the nick. Once inside, the linearized nucleic acid recircularizes. Because Bacillus plasmids replicate by the rolling circle mechanism, the plasmid multimers are in an equilibrium with the monomer form. As a result, recombination between the homologous regions of the multimer results in monomer formation which are capable of segregation upon cell division. Thus, the multimeric form generated in the present invention generally results in a homogeneous plasmid although other Bacillus species that may be made competent for transformation, including, but not limited to, B. licheniformis, B. amyliquofaciens, B. thurigensis, B. alvei, B. anthracis, B. cereus, B. circulans, B. macerans, B. megateriun, B. mycoides, B. pasteurii, B. polymyxa, B. lentus, and B. rotans. The species should be competent, either naturally or via manipulation of the experimental growth conditions.

In addition to Bacillus species, any cell that is transformable with plasmid multimers may be used in the present invention. Microorganisms are preferred. These organisms include, but are not limited to, Vibrio species (see for example Frischer et al., Abstr. Gen. Meet. Am. Soc. Microbiol. 91992) 92 Meet, 390), Penicillium species such as P. chrysogenum (see Cantoral et al., Eur. Congr. Biotechnol. (1987) Vol 1, 512), Streptococcus species such as S. sanguis Challis (see Pozzi et al., FEMS Microbiol. Lett 48:1–2, 189–94 (1987)) and S. mutans (Linder et al., J. Bacteriol. 166:2:658–65 (1986)), and Haemophilus species such as H. influenzae (see McCarthy, J. Mol. Biol. 157:577–596 (1982)).

In addition, the methods of the invention may be used to transform plants with plamid or viral genomic multimers, as is generally described in Howell et al., J. Cell. Biochem. Supp. 7B, 246 (1983).

The methods of the invention utilize two nucleic acids. The first nucleic acid is preferably a double stranded nucleic acid. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. As will be described below, the first nucleic acid may be derived from a plasmid or vector which has been linearized by cleavage within a sequence that is homologous to the second nucleic acid. Thus the first nucleic acid may be either in circular form or in linear form, although it is preferably linearized prior to the PCR manipulation step.

When the first nucleic acid is in a circular form, for example when the first nucleic acid is a plasmid, it has a first end sequence adjacently linked to a second end sequence, with the intervening sequence linked to the first end sequence at one end and the second end sequence at the other. In this embodiment, there is no additional intervening sequence between the first end sequence and the second end sequence.

When the first nucleic acid is in a linear form, it has a first end sequence, and intervening sequence and a second end sequence. Thus, when the first nucleic acid is derived from a plasmid, it is linearized at the junction between the first and second end sequences. In this embodiment, the intervening sequence is linked at one end to the first end sequence and to the second end sequence at the other.

"First" and "second" are not meant to confer an orientation of the sequences with respect to the 5'-3' orientation of a gene. For example, when the first and second end sequences comprise a gene, the first end sequence may be located either 5' to the second end sequence or 3' to it.

The total length of the first nucleic acid may vary, as will be appreciated by those in the art. In a preferred embodiment, the first nucleic acid is a replicating plasmid. Replicating plasmids are well known in the art, and can vary substantially in size. Accordingly, in this embodiment, the first nucleic acid may have a size ranging from about 3 kilobases (kb) to about 50 kb or greater, with from about 3 to about 10 kb being preferred. As will be appreciated in the art, the length of the first nucleic acid will generally be limited to the length of nucleic acid that can be replicated during a PCR reaction. When the first nucleic acid is not derived from a replicating plasmid, for example is to be used for integration into the genome, the first nucleic acid may be smaller. As will be appreciated in the art, it may be necessary to subject a smaller first nucleic acid to additional PCR cycles to achieve an appropriate aggregate size.

Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids. Suitable replicating plasmids for *B. subtilis* are listed on page 92.

In a preferred embodiment, the first and second end sequences comprise all or part of a gene of interest. By "gene of interest" or equivalents herein is meant a gene which is to be transformed into Bacillus species. A gene of interest may be any gene, and includes both heterologous genes and homologous genes. Thus, for example, genes naturally found in one species of Bacillus may be transformed into a different Bacillus species. Alternatively, procaryotic and eukaryotic genes may be introduced into a Bacillus species. Similarly, homologous Bacillus genes may be hooked to different regulatory sequences, for example high-expression promoters or inducible promoters, to allow increased expression of a homologous gene.

Suitable genes of interest encode enzymes such as hydrolases including proteases, carbohydrases, and lipases; isomerases such as racemases, epimerases, tautomerases, or mutases; transferases, kinases and phophatases. The gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

Particularly preferred proteases are subtilisins. Examples of suitable subtilisins include, but are not limited to, the subtilisins from *B. amyloliquefaciens, B. licheniformis, B. subtilis,* and *B. lentus,* including subtilisin DY, subtilisin BPN', subtilisin Carsberg, subtilisin 168, subtilisin amylosaccharitius, mesentericopeptidase, subtilisin thermitase, and proteinase K.

Also included within the definition of subtilisin are variant or mutant subtilisins. A large number of variant subtilisins are known in the art, including variants at the residue positions equivalent to the following positions in *B. amyloliquifaciens:* Tyr6, Ser9, Ile11, Lys12, Gn19, Tyr 21, Thr22, Ser24, Asn25, Asp32, Ser33, Asp36, Ser37, Ser39, Ala45, Gly46, Ala48, Ser49, Met50, Ser53, Glu54, Thr55, Asn56, Pro57, Phe58, His64, His67, Thr71, Asn76, Asn77, Ser87, Ser89, Lys94, Val95, Leu96, Gly97, Asp99, Ser101, Gly102, Glu103, Tyr104, Ile107, Gly110, Ile111, Ile115, Asp120, Val121, Ile122, Met124, Leu126, Gly127, Gly128, Pro129, Leu135, Gly131, Leu135, Asp140, Ala152, Ala153, Gly154, Asn155, Glu156, Gly157, Thr158, Ser159, Gly160, Ser161, Ser162, Ser163, Thr164, Val165, Gly166, Pro168, Gly169, Lys170, Tyr171, Pro172, Ile175, Val180, Ser182, Arg186, Ala187, Phe189, Ser191, Pro194, Glu195, Asp197, Met199, Ser204, Lys213, Tyr214, Gly215, Tyr217, Asn218, Ser221, Met222, His226, Ile234, Leu235, Ser236, Lys237, His238, Trp241, Ser260, Phe261, Tyr262, Lys265, Ile268, or Gln275. See U.S. Reissue 34,606; WO 89/06279; WO 92/10755; and EP 0 549 675 B1, expressly incorporated herein by reference.

Particular preferred genes encode amylases, specifically amylase from *B. licheniformis,* such as those described in PCT/US94/015,553 and WO 94/183,134, hereby both expressly incorporated by reference.

In an alternate embodiment, the intervening sequence of the first nucleic acid comprises at least one gene of interest. In one embodiment, the intervening sequence and the first and second end sequences each contain a gene of interest. In an alternate embodiment, only the intervening sequence of the first nucleic acid contains a gene of interest. In this embodiment, the first and second end sequences are non-coding nucleic acids that have homology to the third and fourth end sequences, as is described below.

In addition to a gene or genes or interest, the intervening sequence of the first nucleic acid may contain a variety of other sequences. For example, when the first nucleic acid is derived from a plasmid, it will have an origin of replication. In some instances, it may have two replication systems, thus allowing it to be maintained in two organisms if necessary, although in a preferred embodiment, the plasmid only contains an origin of replication functional in the organism to be transformed. The first nucleic acid may also include regulatory nucleic acid, such as transcriptional or translational regulatory sequences which are operably linked to the genes of interest. "Operably linked" in this context means that the transcriptional and translational regulatory DNA is positioned relative to the coding sequence in such a manner that transcription and translation are initiated. Generally, this will mean that the promoter and transcriptional initiation or start sequences are positioned 5' to the gene or genes. The transcriptional and translational regulatory nucleic acid will generally be appropriate to the host cell to be transformed; for example, transcriptional and translational regulatory nucleic acid sequences from Bacillus are preferably used in Bacillus.

In general, the transcriptional and translational regulatory sequences may include, but are not limited to, promoter sequences, ribosomal binding sites, transcriptional start and stop sequences, translational start and stop sequences, and enhancer or activator sequences. Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the first nucleic acid may comprise additional elements. For example, when the first nucleic acid is to be integrated into the genome of the Bacillus organism, the first nucleic acid contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating and replicating vectors are well known in the art.

In addition, in a preferred embodiment, the first nucleic acid contains a selectable marker gene to allow the selection of transformed host cells. Selection genes are well known in the art and will vary with the host cell used. Preferred Bacillus selection genes include the genes for chloramphenicol, kanamycin, tetracycline, bleomycin and ampicillin resistance, as well as the genes for macrolide-lincosamid family of antibiotics.

In addition, in a preferred embodiment, for example in the construction of libraries, the intervening sequence will contain a multiple polylinker cloning site (MPCS) or suitable cloning site for the insertion of sequences, as is described below.

Figure 2:
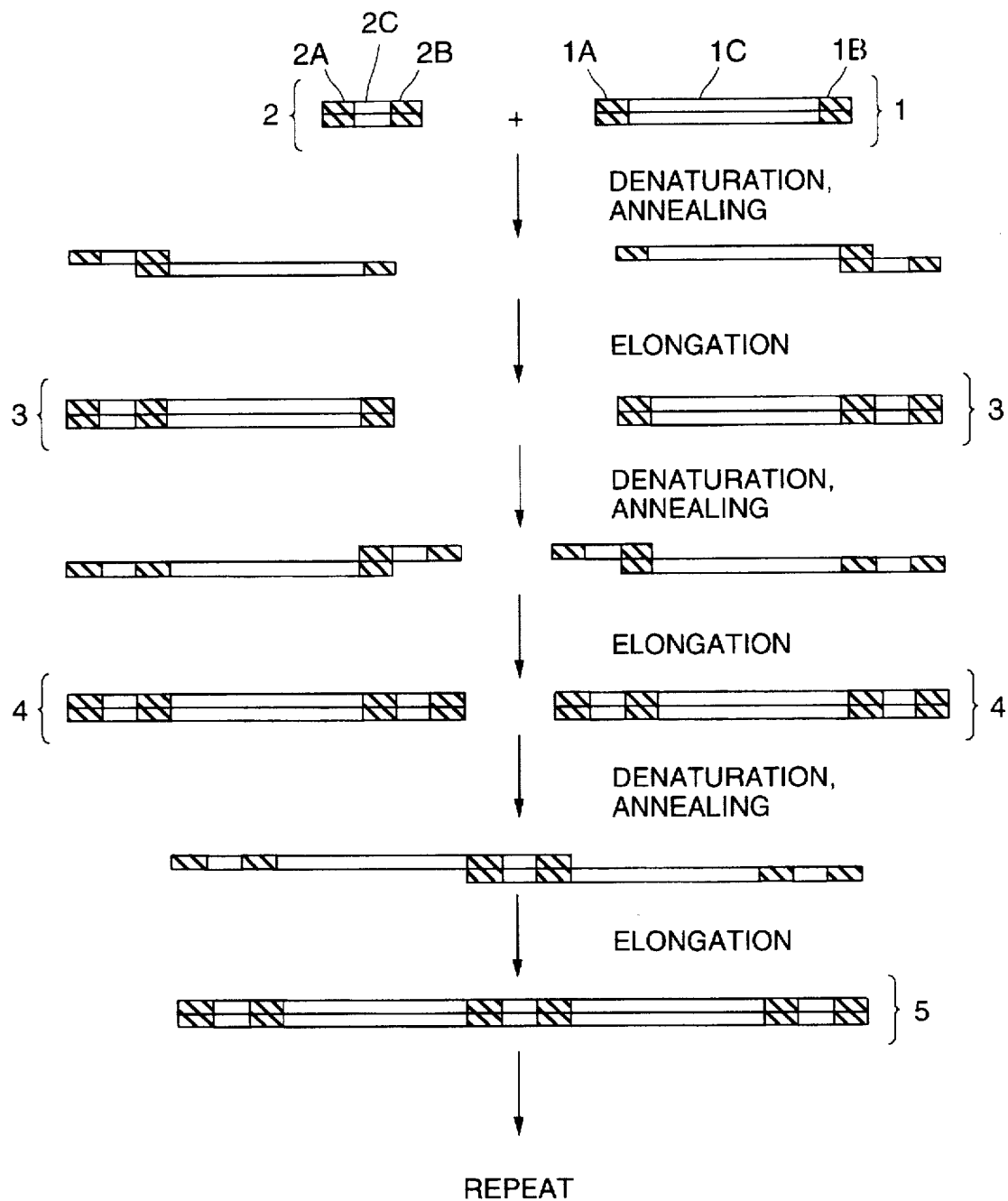
FIG. 2 is a schematic depiction of a method for creating multimers when both the first and the second double stranded nucleic acids have intervening sequences.

The second nucleic acid of the invention comprises a third end sequence and a fourth end sequence. When the third and fourth end sequences comprise a gene, they are preferably contiguous; that is, there is no intervening sequence between the third and fourth end sequence, as is generally depicted in FIG. 1. However, when the third and fourth end sequences are noncoding nucleic acids, it is possible to have an intervening sequence between the third and fourth end sequences, as is generally depicted in FIG. 2. FIG. 2 depicts the first nucleic acid (1) with a first end sequence (1A), an intervening sequence (1C) and a second end sequence (2B). The first nucleic acid is added to the second nucleic acid (2) with a third end sequence (2B), an intervening sequence (2C), and a fourth end sequence (2A). The reaction proceeds as in FIG. 1. In addition to the heteromultimers shown (e.g. multimers containing different intervening sequences), homomultimers may also be formed.

The length of the intervening sequence of the second nucleic acid is preferably short, although, as will be appreciated by those in the art, it may be quite long. What is important is that the length of the sequences between any two homologous regions of the elongated multimer is not too long. As outlined above, the multimers generated by the methods of the invention will generally undergo in vivo homologous recombination to create "plasmid" multimers. The multimer generally should not exceed the acceptable size of stable plasmids. Thus, if the length of both intervening sequences and the four end sequences is too great, efficient transformation may not occur.

The first and third end sequences are homologous, and the second and fourth end sequences are homologous. It should be understood that the two strands which comprise the double-stranded first and second nucleic acids of the invention are denatured during the PCR reaction. When this occurs, a single stranded third end sequence of the second nucleic acid can hybridize to the single stranded first end sequence that has a complementary sequence, and the other single stranded third end sequence can hybridize to the complementary single stranded first end sequence. Similarly, a single stranded fourth end sequence of the second nucleic acid can hybridize to the single stranded second end sequence that has a complementary sequence, and the other single stranded fourth end sequence can hybridize to the complementary other single stranded second end sequence. What is important is that the first and third end sequences, and the second and fourth end sequences, have sufficient homology to allow hybridization, which results in elongation and amplification during the PCR reaction. Accordingly, by "homologous" in this context herein is meant that the two strands of double-stranded end sequences are capable of hybridizing to the complementary end sequence. That is, each strand is sufficiently similar to allow hybridization between complementary strands of each end sequence. "Capable of hybridizing" means that the strands will hybridize under the appropriate conditions. Suitable hybridization conditions are generally those used in PCR reactions, including, low stringency conditions such as annealing at 50°–55° C. in high salt (1–5× SSC) to high stringency conditions such as annealing at 68°–70° C. in low salt 0.1–0.5× SSC); low, moderate and high stringency conditions are known in the art, see for example, Sambrook et al., Molecular Cloning, 2nd Ed., Cold Spring Harbor Laboratory Press, 1989, expressly incorporated by reference. It should be understood that hybridization is also a function of the length of the nucleic acids to be hybridized. That is, the longer the end sequences, the better the hybridization. Thus, in some embodiments, for example in the creation of chimeric genes as outlined below, the end sequences may have low homology but be of sufficient length to allow sufficient hybridization for the generation of multimers. One skilled in the art will be able to easily ascertain whether two end sequences have sufficient homology for hybridization.

Generally, this homology is at least about 60%, that is, 60% of the nucleotides are identical, with at least about 70% being preferred and at least about 80°90% being particularly preferred. However, as described below, the methods of the invention may also be used in the creation of chimeric proteins, in which case the homology may be the minimum that still allows hybridization under the reaction conditions.

As will be appreciated by those in the art, the methods of the invention may also be performed using single stranded nucleic acids, as is known for M13, for example. That is, either or both of the first and second nucleic acids may be single stranded. In one embodiment the first nucleic acid is single stranded, and the first end sequence is capable of hybridizing to one strand of the homologous third end sequence. The second end sequence is capable of hybridizing to one strand of the homologous fourth end sequence. Alternatively, the second nucleic acid is single stranded. In this embodiment, the third end sequence is capable of hybridizing to one strand of the first end sequence, and the fourth end sequence is capable of hybridizing to one strand of the second end sequence. In an additional embodiment, both first and second nucleic acids are single-stranded. The first end sequence is capable of hybridizing to the third end sequence and the second end sequence is capable of hybridizing to the fourth end sequence.

As will also be appreciated by those in the art, it is critical to the invention that the hybridization of a single stranded second nucleic acid to a single stranded first nucleic acid result in a "staggered" or "sticky" or "overlapping" end, to allow the synthesis of multimers of the first nucleic acid. Similarly, every nucleotide of each end sequence must hybridize to a nucleotide of the complementary end sequence (with the exception that some small amounts of preferably non-terminal mismatches may be allowed in the generation of mutations, as is described below). The end sequences should be long enough to allow for good hybridization. Similarly, they should be long enough to allow for selective hybridization to the target end sequence, rather than to a fortuitously complementing sequence within the intervening sequence of the first nucleic acid, for example. Thus, in general, the end sequences should at least be as long as those generally used in PCR. Accordingly, each end sequence is at least about 15 nucleotides, with at least about 50 being preferred, and at least about 200 being particularly preferred.

In a preferred embodiment, as outlined above, the two end sequences comprise a gene. In this embodiment the end sequences may be quite long. Generally, it is desirable to make each end sequence roughly the same length, i.e. half of the gene when the end sequences comprise a gene, although this is not required. Thus, for example, it is possible to have one end sequence be only 5% of the gene and the other end sequence be the other 95%, or any variation thereof. What is important is that the smaller of the end sequences be of sufficient length to allow good hybridization and sequence selectivity.

In a preferred embodiment, the methods are used to faithfully duplicate genes of interest by making first nucleic acid multimers for transformation. That is, identical copies of the first nucleic acid and gene of interest are made, rather than chimeric genes or mutant genes, as is outlined below. In this embodiment, the first and third end sequences are identical, and the second and fourth end sequences are identical. That is, there is perfect complementarity between the single strands of each end sequence that hybridize together. This allows for the faithful reproduction of the sequence. Thus, in a preferred embodiment, the first nucleic acid is a plasmid that has been linearized by cleavage within a gene of interest, such that the two pieces of the gene of interest forms the first end sequence and the second end sequence. The second nucleic acid is generated by cleaving the plasmid at the termini of the gene of interest, such that the second nucleic acid comprises all or part of the gene of interest, with removal of the rest of the plasmid prior to the PCR reaction. In this embodiment, it is not necessary that the second nucleic acid comprise the entire gene of interest.

When faithful duplication of the gene of interest is desired, a large excess of second nucleic acid over the first nucleic acid is used. Thus generally, the first nucleic acid is mixed with the second nucleic acid in a molar ratio of from about 1:1 to about 1:200. In a preferred embodiment, the ratio of first: second nucleic acid is about 1:10 to about 200:1, with about 100:1 being particularly preferred.

In a preferred embodiment, the methods of the present invention are used to transform mutant or variant genes into Bacillus species. This may be done in several ways, and generally involves constructing the mutant genes using well known techniques, and then incorporating the mutant gene or genes into the nucleic acids of the invention, with subsequent multimerization and transformation. In a preferred embodiment, site directed mutagenesis is done on a gene of interest, and then the mutated gene is incorporated into a first or second nucleic acid. Alternatively, mutagenesis libraries may be made, as outlined below.

The mechanism shown in FIG. 1 predicts that it is possible to generate hybrids or chimeric genes, as is outlined below. These chimeric genes are more likely to be formed in the initial stages of PCR multimerization, and may be favored by altering the molar ratio of first nucleic acid:second nucleic acid in the starting reaction. Thus, when chimeric genes are desired, the first nucleic acid is mixed with the second nucleic acid in a roughly equimolar ratio.

In a preferred embodiment, the methods of the invention allow for the creation of chimeric genes from two homologous genes. The general scheme is outlined in FIG. 3. The first nucleic acid (1) is added to the second nucleic acid (2) with a different but homologous gene as the third (2B) and fourth end sequences (2A). After denaturation, annealing and elongation, hybrid genes are formed. The reaction proceeds as in FIG. 1. In this embodiment, the third and fourth end sequences of the second nucleic acid comprises a first gene, and the first and second end sequences of the first nucleic acid comprise a second gene. The sequence of the first and second gene must be similar enough to allow for hybridization between complementary strands to allow the amplification and elongation reaction to proceed. By altering the junction between the end sequences, it is possible to make chimeric genes that vary in the position of the "crossover". That is, if the junction between the end sequences occurs roughly halfway through the gene, then the chimeric gene will have roughly 50% of each gene. If the junction occurs in the first 10% of the gene, then 10% of the chimeric gene will be from the first gene and the other 90% will be from the second gene, and so forth. In this manner it is possible to make chimeric genes that contain any percentage of first gene and second gene, as long as the end sequences are long enough, as outlined above.

As is depicted in the Examples, it is possible to use the same constructs as used in chimeric protocols but favor the creation of one gene over the other by adding the favored gene in a large excess. Thus, the Examples depict the use of two different genes in 100:1 ratio, resulting in a large excess of the first.

The methods of the present invention are also useful in the generation of libraries. This is particularly significant for such species as Bacillus, where the need to passage through another microorganism such as *E. coli* may lead to the introduction of bias and a significant loss of diversity.

In a preferred embodiment, libraries of mutant genes of interest are made. In this embodiment, random mutagenesis is performed as is known in the art. The gene of interest may be on the intervening sequence of the first nucleic acid, or it may be comprise the end sequences of either the first or second nucleic acid.

In a preferred embodiment, random mutagenesis is done on the entire first nucleic acid, using well known PCR mutagenesis techniques. See for example Leung et al., *Technique* 1:11–15 (1989); Cadwell et al., *PCR Methods Applic.* 2:28–33 (1992).

Alternatively, chemical mutagenesis of the nucleic acids or passage of the nucleic acid through hypermutator strains such as those of *E. coli* may be done; these techniques introduce random mismatches into the nucleic acid. Thus, a population of mutant genes is generated to serve as library fragments which are incorporated into the first or second nucleic acid and then multimerized and used to transform a cell such as Bacillus, as is outlined below. The resulting mutants are then analyzed using well known techniques.

In a preferred embodiment, the methods of the invention are used to generate mutagenesis libraries of regulatory sequences. For example, the methods may be used to generate libraries of mutant regulatory sequences for expression in Bacillus. In this embodiment, a regulatory sequence for Bacillus expression is mutagenized using known mutagenesis techniques. The mutant sequences are then incorporated into either a first or second nucleic acid. The nucleic acids are subjected to PCR and then assayed directly for efficacy in Bacillus. Generally, this will be done by linking the mutant regulatory region to a gene whose product is easily assayed, as will be appreciated by those in the art.

In a preferred embodiment, genomic and cDNA libraries are made for transformation into microorganisms such as Bacillus species. The generation of suitable DNA fragments for cloning into a vector is well known for both genomic and cDNA libraries. See for example, Ausubel et al., Ed., *Short Protocols in Molecular Biology*, 2d Ed., Greene Publishing Associates 1992; Sambrook et al., *Molecular Cloning: A Laboratory Manual*, 2d Ed., Cold Spring Harbor Laboratory Press, 1989. A population of library fragments are obtained from genomic digests, from the isolation of mRNA with the synthesis of cDNA nucleic acids using reverse transcriptase, or, as outlined above, from mutagenesis of known genes or sequences. Once generated, the library fragments are inserted into a first nucleic acid of the invention, although, as outlined below, they may also be used as the second nucleic acid, thus generating a population or plurality of first nucleic acid sequences. Preferably, the first nucleic acid has a multiple polylinker cloning site (MPCS) in the intervening sequence, to allow insertion of fragments generated by a variety of restriction enzymes. Thus a variety of first nucleic acids are generated, each containing a different library fragment from the library fragment population in the intervening sequence. These first nucleic acids are added to a population of second nucleic acids to form a PCR reaction mixture, and then the mixture is subjected to the PCR reaction, as outlined below, and the resulting multimers used to transform a cell or microorganism.

In one embodiment, the methods of the present invention are used to isolate nucleic acids which are homologous to known nucleic acids such as a gene of interest, to clone homologous proteins, via methods similar to the creation of chimeric proteins. For example, genomic digests or cDNA libraries are used as either the first or second nucleic acids in the invention. In one embodiment, a known gene of interest is used as the second nucleic acid (the "probe"), and the library fragment is inserted into a first nucleic acid as the first and second end sequences. The library fragment is cleaved to form a first nucleic acid with a first and second end sequence. PCR is done on the first and second nucleic acids in preferably roughly equimolar amounts. If one or more of the library fragments has sufficient homology to hybridize to the second nucleic acid, then multimers are generated. The resulting multimer, in aggregate form, is used to transform Bacillus, for example, which may then be screened for specific characteristics. In an alternate embodiment, the known gene of interest is used as the end sequences of a first nucleic acid, and the library fragment is used as the second nucleic acid. During PCR, as outlined above, if one or more of the library fragments has sufficient homology to hybridize to the second nucleic acid, then multimers are generated, which may then be used to transform a cell or microorganism.

When mutagenesis or DNA libraries are made, or in the generation of chimeric genes, it is likely that a heterogeneous population of first nucleic acids and multimers will be generated. Thus, for example, the generation of libraries results in heterogeneous first nucleic acids, such that the multimers and aggregates will be mixtures of different first nucleic acid sequences, resulting in the transformation of a cell with a variety of different genes. However, as outlined above, the mechanism of uptake and stabilization of nucleic acids within cells such as Bacillus ultimately results in stable monomers with a single gene within the organism. This is due to the fact that plasmid multimers are in an equilibrium with the monomer form, as a result of recombination between the homologous regions of the multimer. Thus, the multimeric form generated in the present invention generates a homogeneous plasmid sequence in the organism, containing a single copy of the gene of interest per plasmid sequence. This appears to be true even if the multimers contain a variety of different genes of interest, for example in the generation of a library or via mutagenesis of a particular gene. In some rare instances, the multimer forms used for transformation that contain different genes may result in organisms that carry more than one gene of interest. However, in these instances, the number of different genes is low (less than five, and usually two) and can be overcome by normal segregation mechanisms for replicating plasmids when grown for a period of time in the host organism.

Once the first and second nucleic acid are generated, they are contacted or mixed together and then subjected to conditions which allow the polymerase chain reaction to occur. By "polymerase chain reaction" or PCR herein is meant a repeated cycle of denaturation, oligonucleotide annealing and primer extension in the presence of a DNA polymerase and deoxynucleotide triphosphates. In the initial cycles, as outlined in the Figures, the first and second nucleic acids are annealed together; in later cycles, annealing also occurs between extended first nucleic acids. As a result of the staggered ends, both nucleic acids serve as primers or templates. An initial denaturation step is only required when double stranded first and/or second nucleic acids are used. Generally the DNA polymerase is a heat stable polymerase such as the Taq polymerase, and the reaction is carried out in a thermal cycler. Suitable PCR conditions and techniques are well known in the art. Preferably, the conditions which permit the polymerase chain reaction to occur are those associated with the PCR machine sold by Perkin-Elmer; see the product literature.

Preferably, elongation times of at least about 3 minutes are used, preferably from about 5 to about 10 minutes are used, as shorter elongation times are less efficacious. This may be due to the fact that the first nucleic acid is generally longer than traditional PCR templates.

PCR is carried out for a number of cycles to make the appropriate multimer length and aggregate size. Covalent multimers comprise at least two copies of the first nucleic acid, and may have many more copies of the first nucleic acid, with at least about 2 to about 20 being preferred, and at least about 5 being particularly preferred. It will be appreciated that the multimers of the invention will vary in size, and that the reaction product from PCR will be a heterogeneous mixture of multimers of various sizes.

Accordingly, at least about 3 to about 10 PCR cycles are preferred, with about 5 to about 40 being particularly preferred, and about 25 to about 35 being especially preferred. As is outlined below, the PCR reaction should continue until the multimeric and/or aggregate product of the reaction is large enough to efficiently transform the cell. This size may vary with the cell to be transformed, as the optimum multimer/aggregate size for particular cells may vary. This is easily determined using well known techniques, as is outlined below.

Figure 4:
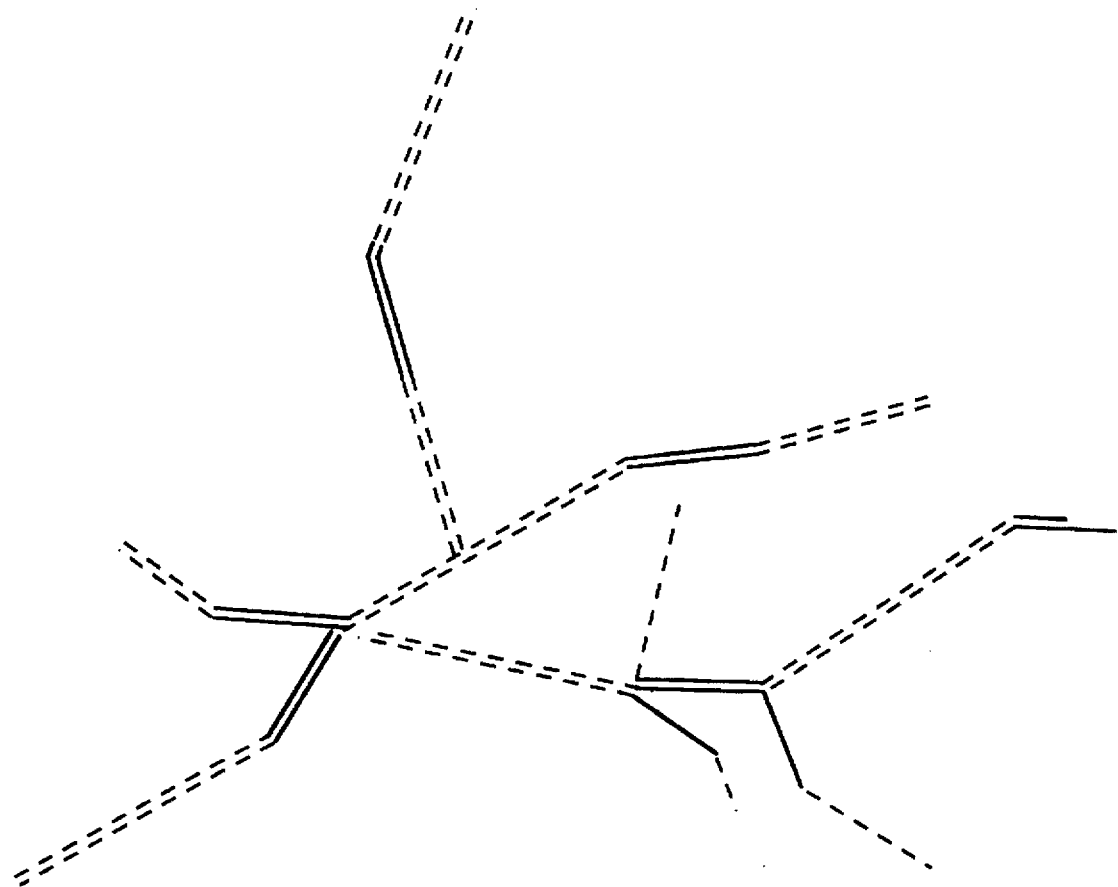
FIG. 4 is a schematic depiction of the multimeric aggregates formed by the methods of the present invention.

In addition to covalent multimers, it appears that the PCR reaction results in the formation of aggregates. That is, as is schematically depicted in FIG. 4, a number of multimeric elongation products may associate to form aggregates. The size of these aggregates may vary significantly.

Once a sufficient number of PCR cycles have been completed, the multimer/aggregate product of the reaction is used to transform a cell such as a microorganism. In one embodiment, the multimers are purified prior to transformation, using well known techniques. In a preferred embodiment, the multimers need not be purified or isolated prior to transformation.

Transformation systems are known in the art for a wide variety of the host organisms used in the present invention. In a preferred embodiment, Bacillus species are used, and transformation systems are well known for Bacillus; see Molecular Biological Methods for Bacillus, Ed. Harwood, supra, in particular pages 33–35 on transformation, expressly incorporated herein by reference.

The transformation efficiencies of the methods of the present invention are quite high, ranging from about $10^3$ to about $10^6$ transformants per µg of DNA, with $10^5$ to $10^6$ transformants per µg of DNA being preferred. Since generally the PCR reaction gives 5 to 10 µg of DNA, only a small fraction of the PCR reaction mix is used to transform competent cells.

Once transformed, the microorganisms may be cultured to express the gene of interest, and screened, if necessary. Generally, the host organism is grown at the appropriate conditions to induce or cause expression of the protein encoded by the gene of interest. The conditions appropriate for protein expression will vary with the choice of the expression vector and the host cell, and will be easily ascertained by one skilled in the art through routine experimentation. For example, the use of constitutive promoters will require optimizing the growth and proliferation of the host cell, while the use of an inducible promoter requires the appropriate growth conditions for induction. Culture conditions are generally known in the art for the wide variety of appropriate host organisms.

Transformed organisms are selected on the basis of the presence of the first nucleic acid. Selection may be done as a result of the presence of the gene of interest, for example, by screening for a particular gene product, as is outlined in the Examples. Alternatively, selection may be accomplished on the basis of a selection marker gene of the first nucleic acid, such as an antibiotic resistance gene.

In one embodiment, no selection step is necessary, as the transformation efficiencies of the methods of the invention are so high. However, in some organisms, replicating plasmids are not stably maintained in the absence of some selective pressure, and thus growth on selection media is preferred.

In a preferred embodiment, the protein product of the gene of interest may be isolated or purified. In a preferred embodiment, for example when the gene product is secreted in high amounts, it may only be necessary to remove the cells, for example by centrifugation or filtration. In alternate embodiments, the gene product may be further purified using well known techniques, depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the gene product may be purified using a standard anti-protein antibody column. Ultrafiltration and diafiltration techniques, in conjunction with protein concentration, are also useful.

For general guidance in suitable purification techniques, see Scopes. R., Protein Purification, Springer-Verlag, NY (1982). The degree of purification necessary will vary depending on the use of the gene product. In some instances no purification beyond cell separation will be necessary.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLE 1

Replacement of a Gene

Figure 5:
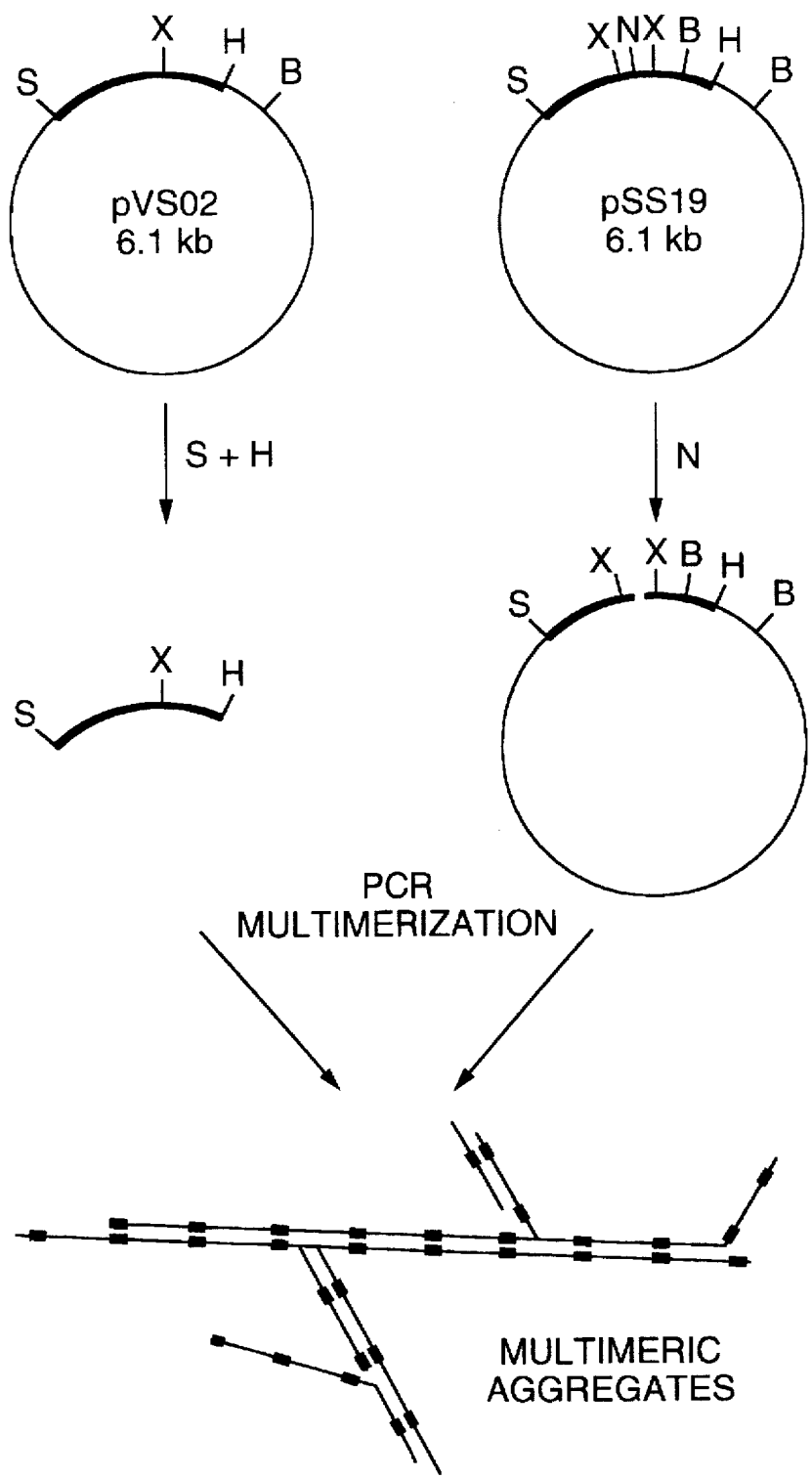
FIG. 5 depicts the method described in the examples. The highlighted protease gene in pSS19 was replaced by the homologous gene from pVS02. S, SalI; X, XbaI; H, HindIII; B, BamHI; N, NarI.

In order to test the method depicted generally in FIG. 1, the protease gene in the vector pSS19 was replaced by the homologous gene contained in pVS02. This process is illustrated in FIG. 5. The protease-coding gene was isolated from pVS02 as a 1115 bp SalI/HindIII fragment. The vector pSS19 was linearized by NarI digest. Insert and vector were mixed in a molar ratio of 100:1 and subjected to PCT using rtth DNA polymerase. Fluorescence detection indicated that about 100 ng/µl DNA was obtained. A major fraction of the resulting product did not run in a 1% agarose gel (see FIG. 6, lane 4) indicating a very large apparent molecular weight of the product. The PCR multimers efficiently transformed competent Bacillus subtilis BG2864 and $3\times10^6$ transformants per µg of DNA were obtained. About 98% of the transformed cells formed large halos on agar plates containing skim milk which indicated that most transformed cells contained a fully functional protease gene. The other colonies showed either no halos or halos of reduced size. Plasmid DNA was isolated from 25 of these colonies. 24 of the clones gave a restriction pattern identical to pVS02 (FIG. 6). This indicates that the background of vector sequence in the multimers is very low. The 100-fold excess of the gene fragment over the vector sequence that is used for the multimerization ensures that very little vector background is obtained. Restriction digest of the PCR multimers confirms that a large fraction of the material can be cleaved into fragments of the expected size (FIG. 6, lane 5). No band which would have indicated contamination with the vector sequence could be observed.

One clone which produced a normal sized halo appeared to be a hybrid between both homologous genes, based on a different restriction pattern digest. The mechanism shown in FIG. 3 predicts that such hybrids will be formed during the initial stages of PCT multimerization. Obviously, their percentage in the final product is low due to the large excess of the gene fragment over the vector. By using equimolar ratios of insert and vector it is possible to deliberately generate hybrid genes between homologous genes.

Figure 3:
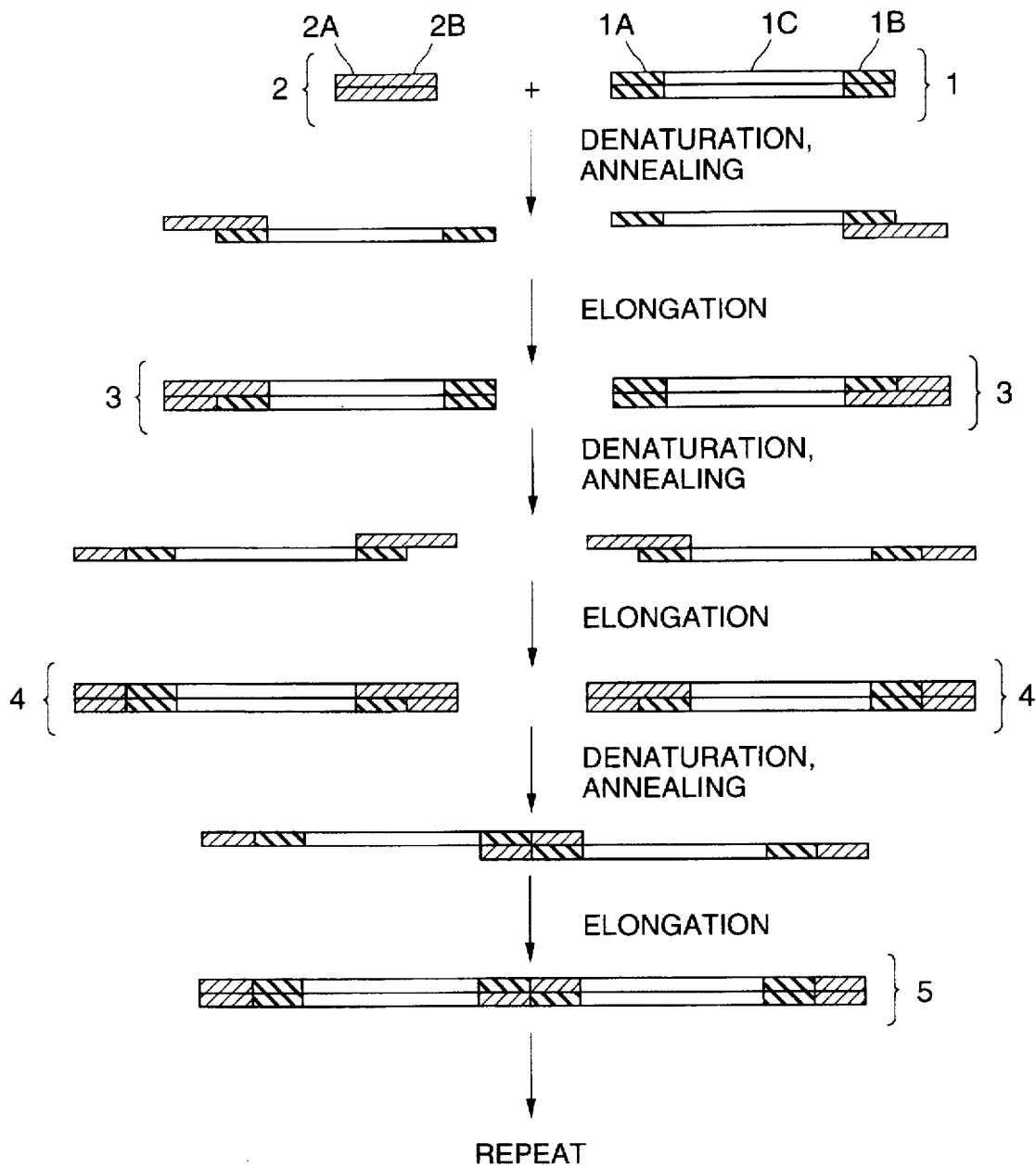
FIG. 3 is a schematic depiction of a method for creating chimeric proteins using the nucleic acids of the invention.

Plasmid DNA from 5 transformants which did not form halos on skim milk plates were analyzed. Three clones gave restriction patterns which were indistinguishable from pVS02 (FIG. 3, lane 7). Most likely, these clones contain mutations in the protease gene or in its promoter which were introduced during the PCR multimerization. No plasmid DNA could be isolated from the other two clones.

No rearrangement or deletion was observed in any of the analyzed clones. It appears that the rec system of Bacillus subtilis is able to efficiently reconstruct the plasmid molecules from the PCR generated multimers. Controls lacking either the gene fragment or the vector did not result in detection of any multimers by agarose gel electrophoresis and no transformants could be obtained from the resulting products.

EXAMPLE 2

Random Mutagenesis of a Gene

The large number of transformants obtained from the PCR multimers makes the technique particularly attractive for the generation of random libraries of a gene. The protease gene was amplified in pVS02 with a set of primers directly flanking the gene under conditions of very low polymerase fidelity (Cadwell, 1992, supra). Residual primers were removed and the PCR fragment was multimerized using linearized vector as described herein. Again about 100 ng/µl of multimers were obtained and the transformation efficiency was similar. However, 84% of the transformants did not form halos on skim milk. Many other clones formed halos of reduced size. Example 1 demonstrated that few mutations are introduced during PCR multimerization. Consequently, most of the non-halo forming clones obtained in this experiment should carry mutations resulting from the mutagenic PCR. These mutation s must be located within the protease gene to result in a lack of halo formation. Analysis of plasmid DNA from 10 of these clones showed identical restriction patterns to pVS02 for all of them. This verified that no rearrangements or deletions occured during the multimerization process. It is also important to note that the random mutations in the protease gene do not appear to have any adverse effect on the efficacy of the subsequent multimerization.

It is known that some DNA polymerases including the taq polymerase add an unpaired A to the 3' end of PCR products (Clark, 1988, *Nucleic Acid Res.* 16:9677–9686). Therefore, primers were designed for PCR mutagenesis such that the unpaired A would not lead to a mismatch during the subsequent multimerization. However, in the initial studies a different pair of primers was used and the polymerase-added A should have caused a mismatch in the following reaction. For both sets of primers an identical yield of PCR multimers and similar numbers of transformants were obtained. Furthermore, the frequency of mutations in the clones did not appear to be significantly affected. We assume therefore that a 3' mismatch can be efficiently reparied by the exonuclease activity which is contained in the enzyme mixture used for the multimerization.

EXAMPLE 3

Characterization of the PCR Multimers

No synthetic primers are added during the plasmid multimerizations and, consequently, all newly formed DNA must result from elongation of the fragment and the vector which are contained in the reaction mixture. Using fluorescence, it was determined that a multimerization reaction using 3 ng/µl yields about 100 ng/µl of product. Using this information, an average chain length of 30 kbp was calculated for the multimers, corresponding to pentamers of the plasmid. However, DNA of that size would migrate into a 1% agarose gel, which contradicts the experimental observation (see FIG. 6, lane 4). Accordingly, it appears that aggregates of multimers are formed during the last annealing steps of the multimerization due to the variable length of the strandes and their presumably staggered alignment (see FIG. 4 and the bottom of FIG. 5). It is interesting to note that these aggregates are so efficient in transforming competent Bacillus subtilis. When the plasmid multimers were diluted 100 fold, heated and reannealed, an 80-fold drop in transformation efficiency was observed (data not shown).

EXAMPLE 4

Direct Transformation of *B. subtilis* with an amylase gene

Various regions of the gene of α-amylase from *B. licheniformis* have been amplifed by PCR. The product was multimerized using a vector which carried the same gene in pHP13 (pHP13 is a low-copy number plasmid, as opposed to the high copy number plasmids used to clone the protease genes). The multimerization products were used to transform competent *B. subtilis* with high efficiency.

Having described the preferred embodiments of the present invention, it will appear to those of ordinary skill in the art that various modifications may be made to the disclosed embodiments, and that such modifications are intended to be within the scope of the present invention.

I claim:

1. A method of transforming a cell comprising:
   a) contacting
      i) a first linear nucleic acid comprising a first end sequence, a second end sequence and an intervening sequence; and
      ii) a second linear nucleic acid comprising a third end sequence homologous to said first end sequence and a fourth end sequence homologous to said second end sequence;
   to form a polymerase chain reaction mixture;
   b) subjecting said polymerase chain reaction mixture to conditions which permit amplification by the polymerase chain reaction for at least 3 cycles;
   c) transforming said cell with the product of step b).

2. A method according to claim 1 wherein said first nucleic acid comprises a linearized plasmid.

3. A method according to claim 1 wherein said first end sequence and said second end sequence comprise a gene when ligated together.

4. A method according to claim 1 wherein said intervening sequence comprises a gene.

5. A method according to claim 1 wherein said first end sequence is identical to said fourth end sequence and said second end sequence is identical to said third end sequence.

6. A method according to claim 1 wherein said polymerase chain reaction mixture comprises a 100 fold excess of said second nucleic acid over said first nucleic acid.

7. A method according to claim 1 wherein said polymerase chain reaction mixture comprises roughly equal amounts of said first and second nucleic acids.

8. A method according to claim 1 wherein said cell is a microorganism.

9. A method according to claim 1 wherein said cell is a Bacillus species.

10. A method according to claim 1 wherein said cell is *B. subtilis*.

11. A method according to claim 1 further comprising the steps of
   d) selecting said transformed cell by selecting for the presence of the first nucleic acid.

12. A method according to claim 1 further comprising the steps of
   e) culturing said transformed cell under conditions which express a gene product of said first nucleic acid.

13. A method according to claim 12 further comprising the steps of f) isolating said gene product from said transformed cell.

14. A method according to claim 1 wherein prior to step a), a circular first nucleic acid is cleaved at the junction between said first and second end sequences to form a linear first nucleic acid.

15. A method according to claim 1 wherein said first nucleic acid is single-stranded, said first end sequence is capable of hybridizing to one strand of said homologous third end sequence, and said second end sequence is capable of hybridizing to one strand of said homologous fourth end sequence.

16. A method according to claim 1 wherein said second nucleic acid is single-stranded, said third end sequence is capable of hybridizing to one strand of said homologous first end sequence, and said fourth end sequence is capable of hybridizing to one strand of said homologous second end sequence.

17. A method according to claim 1, wherein said first and second nucleic acids are single stranded, and said first end sequence is capable of hybridizing to said third end sequence, and said second end sequence is capable of hybridizing to said fourth end sequence.

18. A method of generating nucleic acid multimers comprising:
 a) contacting
  i) a first linear nucleic acid comprising a first end sequence, a second end sequence and an intervening sequence; and
  ii) a second linear nucleic acid comprising a third end sequence homologous to said first end sequence and a fourth end sequence homologous to said second end sequence;
 to form a polymerase chain reaction mixture;
 b) subjecting said polymerase chain reaction mixture to conditions which permit amplification by the polymerase chain reaction for at least 3 cycles.

19. A nucleic acid multimer made by the method of claim 18.

20. A method of making a chimeric nucleic acid comprising:
 a) contacting
  i) a first nucleic acid comprising a first end sequence, a second end sequence and an intervening sequence; and
  ii) a second nucleic acid comprising a third end sequence homologous to said first end sequence and a fourth end sequence homologous to said second end sequence;
 to form a polymerase chain reaction mixture, wherein the sequence of said third end sequence has at least one different nucleotide than the sequence of said first end sequence; and
 b) subjecting said polymerase chain reaction mixture to conditions which permit amplification by the polymerase chain reaction for at least 3 cycles.

21. A method according to claim 20 further comprising the step of c) transforming a cell with the product of step b).

22. A method according to claim 21 further comprising the step of d) culturing said transformed cell under conditions which permit the production of a chimeric gene product of said first nucleic acid.

23. A method according to claim 22 further comprising the steps of e) isolating said gene product from said transformed cell.

24. A method according to claim 21, wherein said cell is a Bacillus species.

25. A method according to claim 24, wherein said Bacillus species is *B. subtilis*.

26. The chimeric nucleic acid multimer made by the method of claim 20.

27. A method of generating a library in a microorganism comprising:
 a) generating a plurality of first nucleic acids wherein said nucleic acids function as vectors each comprising a first end sequence, an intervening sequence, and a second end sequence, wherein said plurality of first nucleic acids comprise a population of library fragments,
 b) contacting said plurality of first nucleic acids with a second nucleic acid comprising third and fourth end sequences homologous to the first and second end sequences, respectively, of at least one of said first nucleic acids to form a polymerase chain reaction mixture;
 c) subjecting said polymerase chain reaction mixture to conditions which permit the polymerase chain reaction for at least 3 cycles;
 d) transforming said microorganism with the products of step c) thereby generating a library.

28. A method according to claim 27 wherein said library fragments are contained within the intervening sequence of said first nucleic acids.

29. A method according to claim 27 wherein said first and second end sequences comprise said library fragments.

30. A method according to claim 27 wherein said population of library fragments comprise a population of mutant genes.

31. A method according to claim 30 wherein said mutant genes are contained within the intervening sequence of said first nucleic acids.

32. A method according to claim 30 wherein said first and second end sequences comprise said mutant genes.

33. A method according to claim 30 wherein said gene is a protease gene.

34. A method according to claim 33 wherein said protease is subtilisin.

35. A method according to claim 30 wherein said gene is amylase.

36. A library made according to the method of claim 27.

37. A mutant library made according to claim 30.

\* \* \* \* \*